United States Patent [19]

Smith et al.

[11] Patent Number: 5,020,671

[45] Date of Patent: Jun. 4, 1991

[54] METHOD AND APPARATUS FOR OPTIMUM SELF-EXAMINATION OF BREASTS BY USERS OF BIRTH CONTROL PILLS

[76] Inventors: Raleigh A. Smith, 211 Medical Dr., Ste. 3; Alfred Kager, Llano Route, Box 77-A, both of Fredericksburg, Tex. 78624-4469

[21] Appl. No.: 409,405

[22] Filed: Sep. 19, 1989

[51] Int. Cl.$^5$ .............................................. B65D 75/54
[52] U.S. Cl. .................................. 206/534; 128/737; 206/459
[58] Field of Search ............... 128/630, 737, 774, 898; 206/459, 528, 531, 532, 534, 538; 434/267

[56] References Cited

U.S. PATENT DOCUMENTS

| | | | |
|---|---|---|---|
| 611,136 | 9/1898 | Mason | 206/538 |
| 2,790,587 | 4/1957 | Contant | 206/532 |
| 3,302,775 | 2/1967 | Finkelston, Jr. et al. | 206/434 |
| 3,381,808 | 5/1968 | McGraw, II | 206/534 |
| 3,397,671 | 8/1968 | Hartman, Jr. et al. | 206/534 |
| 3,402,808 | 9/1968 | Yannuzzi | 206/534 |
| 4,134,218 | 1/1979 | Adams et al. | 434/267 |
| 4,534,468 | 8/1985 | Nuckols et al. | 206/459 |
| 4,553,670 | 11/1985 | Collens | 206/534 |
| 4,736,849 | 4/1988 | Leonard et al. | 206/534 |
| 4,889,238 | 12/1989 | Batchelor | 206/534 |
| 4,955,481 | 9/1990 | Novinski et al. | 206/534 |

OTHER PUBLICATIONS

"Betsi Breast Teaching Model", Department of Educational Services, ORTHO, no month, 1973.

Primary Examiner—Jimmy G. Foster
Attorney, Agent, or Firm—Donald R. Comuzzi

[57] ABSTRACT

A method and associated apparatus in aid of optimum self-examination of the breast by women for early detection of breast cancer.

9 Claims, 2 Drawing Sheets

METHOD AND APPARATUS FOR OPTIMUM SELF-EXAMINATION OF BREASTS BY USERS OF BIRTH CONTROL PILLS

BACKGROUND OF THE INVENTION

This invention relates to a method and associated apparatus in aid of optimum self-examination of the breast by women for early detection of breast cancer. The importance of monthly self-examination by women to detect breast tumors is universally accepted and recommended by the medical profession. Early detection of breast cancer leads to significantly higher chances of survival for the breast cancer patient because treatment, such as surgery or chemotherapy, is most effective when initiated at the early stages of the carcinoma.

The method and associated products of the present invention ties the clinically recommended monthly self-exam to the female menstruation cycle. The menstruation cycle is used as an "internal clock" with which a woman can regulate self-examination of her breasts. Normally, a woman's breasts are the least enlarged (that is to say smallest in size) and softest seven to twelve days after the onset of menstrual bleeding. Breast tumors usually present themselves as lumps of various sizes embedded in the soft tissues of the breast with a relatively hard and bumpy skin surface in relation to surrounding skin covering a woman's chest.

Since the female breast is smallest and softest seven to twelve days after the onset of bleeding, breast tumors are easier to detect within this "time window." During this period, the surrounding soft tissue is much softer than the cancerous lump, and the tumor is presented more prominently because of the smaller size of the overall breast. Because the lump is easier to palpitate during this period, the clinically suggested optimum time for self-exam is the six day "window" in the woman's menstrual cycle.

However, such recommendations, like other medical advice, meets with compliance problems. The problem that is often clinically encountered is encouraging women to remain on such a regulated course of self examination. Women have different cycles, different levels of social and educational backgrounds, and different motivations and health goals. These factors all lead to less than strict compliance with regular monthly self-examinations. Continuous monthly self-exams are usually altogether forgotten by the time of the next appointment with the gynecologist.

There has been a particular need for a product and method that can aid women in regulating self-examinations based on external criteria. There is a need for a systematic method whereby a woman can set a regular schedule of self-exam depending on set, repeatable, external factors. The external criteria set by the present invention, uses a schedule that coincides with conditions when tumors can best be detected by self-examination. This method increases a woman's chance of detecting cancer at an early stage by providing reminders to enhance compliance with recommended monthly self-exams.

Female hormone supplements (commonly referred to as birth control pills) can be such an external system used as constant reinforcers of the need for self-examination. Birth control pills regulate a woman's menstruation cycle by controlling levels of the hormones estrogen and progesterone to prevent implantation of a fertilized embryo onto a female's womb. This regulation is utilized as the basis for this invention.

Most birth control pills contain estrogen, some in larger relative quantities and others in relative combinations with progesterone. Medical research has linked breast cancer with the use of estrogen as a female hormone supplement. Thus, users of estrogen containing birth control pills have a relatively higher risk of developing breast cancer. This invention will increase the chances of early detection of tumors in women who use estrogen containing birth control pills by increasing compliance with the recommended monthly self-exams.

SUMMARY OF THE INVENTION

The present invention discloses a method whereby women can self-examine their breasts at optimum periods in the menstruation cycle to increase the chances of tumor detection based on an external system. One such method is to color code packages of birth control pills. The birth control pills or the slots in the package containing the pills are color coded so that a woman is prompted to do a self-exam when the relevant color comes up. The color codes are made to coincide with the seven to twelve days after the onset of bleeding when the woman's breast are the smallest and softest. Thus, the color coded pill or pill packet alerts the taker to do a self-exam at the point in time during her controlled cycle when a tumor will most likely be detected.

High incidence of breast tumors have been linked to birth control pills with high estrogen content. The present invention is an additional safeguard to women on pills with high estrogen content for early cancer detection.

Ordinarily, a birth control pill package contains either 28 pills (21 hormone pills and 7 placebos), or just 21 hormone pills. One pill is taken each day with the 28 pill package, or 21 pills are taken daily with seven days of taking nothing in the alternate package. Because of the wide range of products available on the market, some pill packages vary from the above. However, with any package system, break-through bleeding occurs one to three days after the taking of the last hormone pill. For women on the pill, the optimum conditions of breast self-exam occurs seven to twelve days after taking the last hormone pill.

Therefore, the pills themselves or the packaging containing the pills are color coded or labeled to indicate the seven to twelve days after the time when the last hormone pill is taken.

A preferred embodiment of this invention is a method of reminding users of birth control pills to do monthly breast self-examinations on days of the menstrual cycle which are most likely to allow detection of abnormalities by use of colors on pills which are taken on the six days of the cycle which are optimum for self-exam.

Another embodiment of the invention is the use of labeling on, or color coding of, the packaging itself adjacent to slots wherein pills are contained instead of color coding the pills.

Another embodiment is a reminder packet that can be modifications of existing birth control pill packaging on the market which calls attention to the optimum days for self-exam. This is done by imprinting messages or color coding adjacent to relevant slots containing pills in packages presently on the market. Adhesive labels with messages or color coding inserted onto packages presently available to the consuming public can accomplish the same goal.

Another embodiment modifies the shape, color, or size of the appropriate pill already on the market to prompt the user to do a self-exam on the day the modified pill is taken.

Another embodiment would designate only one day within the six day "window" for the female taking the pill to do a self-exam.

Other objects, features and advantages of the invention will become evident in light of the following detailed description considered in conjunction with the referenced drawings of preferred exemplary embodiments according to the present invention.

DETAILED DESCRIPTION OF THE PREFERRED EMBODIMENTS

Figure 1:
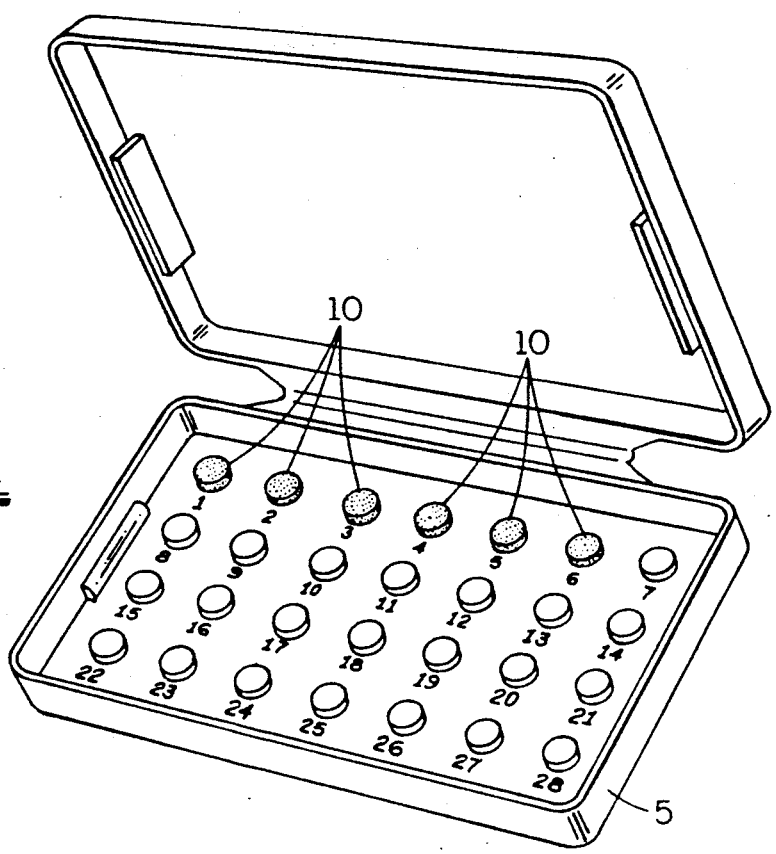
FIG. 1 is a variant of conventional packaging containing female hormone supplements with a preferred embodiment depicted by dark shading of pills that are taken on days when breasts are to be self-examined.

With reference to the drawings, the preferred embodiments of the present invention will be described. One variation of a conventional female hormone supplement dispenser is depicted in FIG. 1. The packaging 5 usually contains twenty eight pills. The six shaded pills 10 are designated in this embodiment as the six days on which the female taking the pills is to perform self-examination of her breasts to detect abnormalities. The shading on the six pills 10 depict the color coding which is encoded and explained in accompanying brochures or the outer wrapper of the packaging.

The shaded pills 10 can also represent modifications of existing pills on the market. The modifications can be solely coloring of the pills, changes in size or shape of the pills, or any combinations thereof. All modifications will have accompanying brochures or instructions on the outer wrappings to explain the modifications as reminders for breast self-exam.

Figure 2:
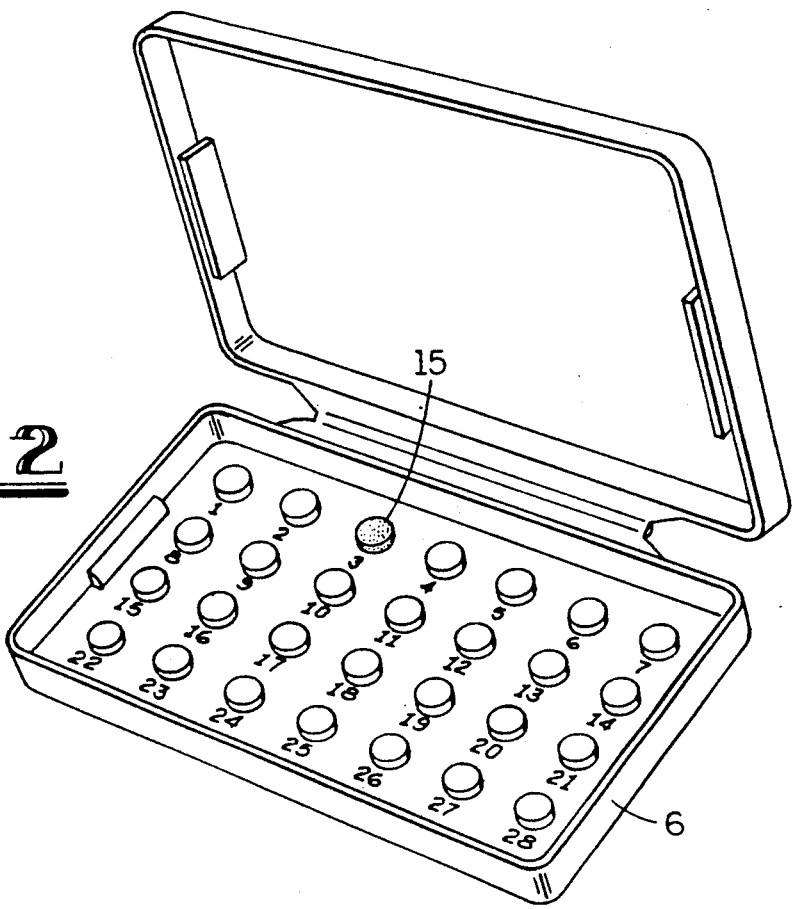
FIG. 2 is another embodiment wherein one pill is shaded indicating the day when the female should do her monthly self-exam.

All six pills 10, representing the six day optimum "window" for ideal monthly self-exam, need not be color coded or modified. Five or less pills can be distinguished from the rest. FIG. 2 depicts another embodiment wherein the conventional female hormone supplement dispenser 5 contains only one pill 15 which is distinctive from the other pills and depicted as a single shaded pill. In this embodiment, the woman taking the single distinctive pill will be prompted to do her monthly self-examination of her breasts on the day she takes that pill.

Similarily, five, four, three, or two pills can be distinguished, and the woman taking the different pills is reminded to do breast self-examinations on the day she takes them.

Figure 3:
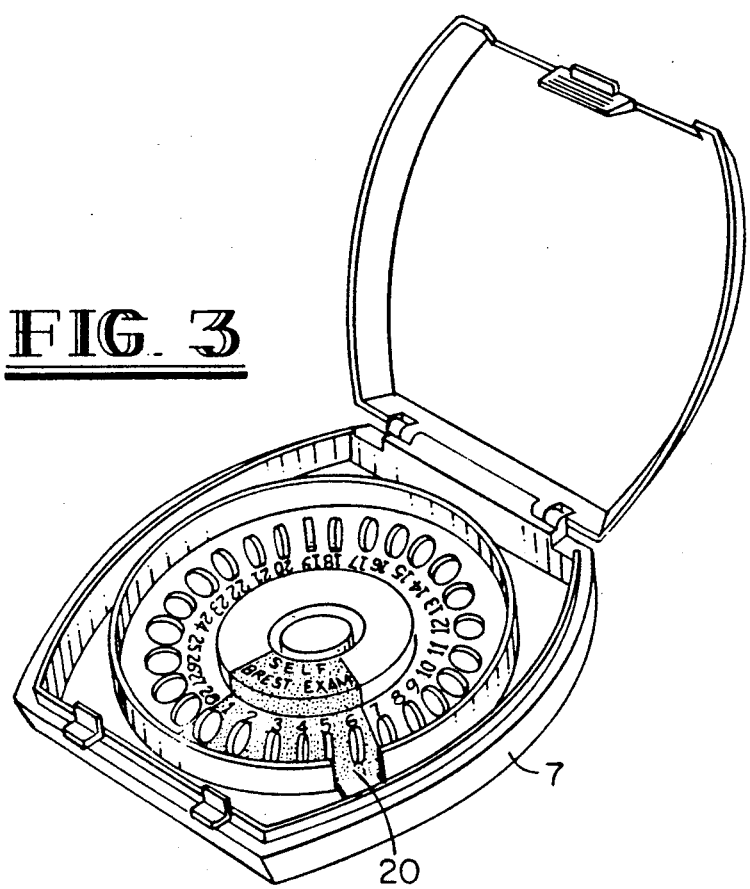
FIG. 3 is another embodiment which shows another variant of conventional packaging depicting the use of imprinted messages directly on the packaging containing the pills.

FIG. 3 illustrates another embodiment of this invention depicting the use of another variation of conventional female hormone supplement dispenser 7 which is imprinted with a reminder message 20 directly onto the packaging surface. The imprinted message is placed directly adjacent the designated pills. This imprinting can be used in lieu of modifying the pills as described above or used in combination with the said modifications. As in the above described embodiments, these modified packaging will have accompanying brochures or instructions on the outer wrappings to explain the modifications as reminders for breast self-exam.

Also, as in the above described embodiments, the packaging depicted in FIG. 3 can be modified to distinguish five, four, three, or two pills, or only one pill as reminders to the female to do like numbers of daily self-exams during that period of her menstruation cycle.

Figure 4:
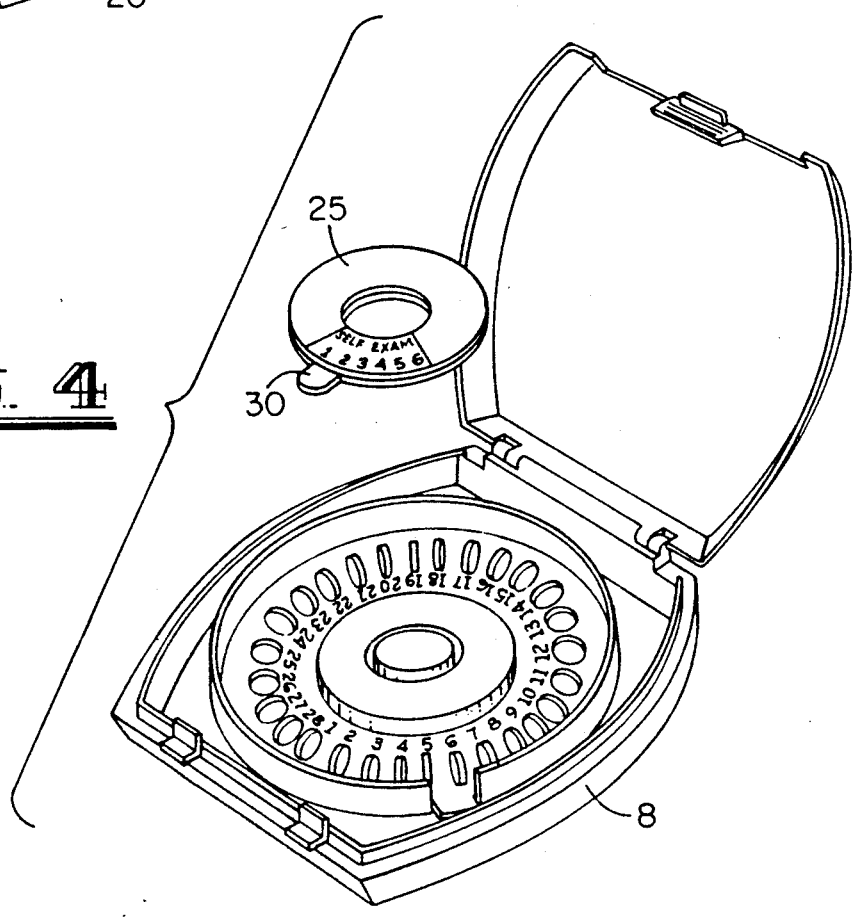
FIG. 4 is another embodiment illustrating the use of adhesive labels or the like which are designed to be superimposed on packaging already available on the market.

FIG. 4 illustrates the use of adhesive labeling or similar devices to accomplish the same goals as in the above described embodiments. An illustrative adhesive label 25 with peelable backing 30 can be printed with appropriate messages. The labels are designed to fit any existing birth control pill packets on the market. Once the peelable backing 30 is removed, the label is placed onto to packaging 8 with the desired prompt messages aligned immediately adjacent to designated pills or pill.

Thus, the present invention is well suited to carry out the objects and attain the ends and advantages mentioned above as well as those inherent therein. While the preferred embodiments of the present invention have been described for the purposes of this disclosure, changes in the design and arrangements of features can be made by those skilled in the art, which changes are encompassed within the spirit of this invention as defined by the appended claims.

What is claimed is:

1. A method for women taking female hormone supplements to regulate monthly breast self-examinations, which comprises:
    providing a female hormone supplement monthly dispenser having:
        a plurality of hormone supplement pills, and imprinted messages on said female hormone supplement dispenser immediately adjacent only a portion of said plurality of hormone supplement pills; and
    prompting the female taking said hormone supplement pills with said messages to self-examine her breasts on days designated by said imprinted messages.

2. The method of claim 1 wherein said portion of said plurality of hormone supplement pills has distinctive color that is different from the remainder of said plurality of hormone supplement pills.

3. The method of claim 1 wherein said portion of said plurality of hormone supplement pills is of distinctive size that is different in dimension from the remainder of said plurality of hormone supplement pills.

4. The method of claim 1 wherein said portion of said plurality of hormone supplement pills is of distinctive shape that is of different conformation from the remainder of said plurality of hormone supplement pills.

5. A female hormone supplement dispenser, comprising:
    a plurality of hormone supplement pills;
    a plurality of pills distinctive from said hormone supplement pills; and
    messages imprinted on said dispenser adjacent only said plurality of distinctive pills the female taking said hormone supplement pills to self-examine her breasts on days said distinctive pills are taken.

6. The dispenser of claim 5 wherein said distinctive pills are of a different color to said plurality of hormone supplement pills.

7. The dispenser of claim 5 wherein said distinctive pills are of a different size to said plurality of hormone supplement pills.

8. The dispenser of claim 5 wherein said distinctive pills are of a different shape to said plurality of hormone supplement pills.

9. A female hormone supplement monthly dispenser, comprising;
a plurality of hormone supplement pills; and
a labeling means inserted into said female hormone supplement dispensers, comprising:
   a panel means imprinted with messages, said imprinted messages prompting the female taking said hormone supplement pills to self-examine her breasts on days designated by said imprinted messages, and wherein
   said panel means is superimposed over said female hormone supplement dispenser such that said imprinted messages are immediately adjacent only a portion of said hormone supplement pills.

* * * * *